United States Patent [19]

Bellini et al.

[11] Patent Number: 4,547,516

[45] Date of Patent: Oct. 15, 1985

[54] ANTISECRETORY AGENTS DERIVED FROM MELDRUM'S ACID

[75] Inventors: Francesco Bellini, Mount Royal; Jehan Bagli, Kirkland, both of Canada

[73] Assignee: American Home Products Corporation, New York, N.Y.

[21] Appl. No.: 543,713

[22] Filed: Oct. 20, 1983

[51] Int. Cl.$^4$ .................. A61K 31/38; A61K 31/40; C07D 233/54

[52] U.S. Cl. .................. 514/385; 514/444; 514/452; 549/50; 549/60; 549/274; 548/335

[58] Field of Search .................. 549/60, 274, 50; 548/335; 424/269, 275, 279; 514/385, 444, 452

[56] References Cited

U.S. PATENT DOCUMENTS 4,118,557 10/1978 Lesher .................. 549/274

OTHER PUBLICATIONS

U. Herzog and H. Reinshagen, Eur. J. Med. Chem.—Chim. Ther., 11 415 (1976).
F. P. Colona et al., J. Chem. Soc., Perkin Trans., 2, 279 (1978).
J. Sandstrom and U. Sjostrand, Tetrahedron, 34, 371 (1978).
U. Sjostrand and J. Sandstrom, Tetrahedron, 34, 3305 (1978).
J.-P. Celerier et al., J. Org. Chem., 44, 3089 (1979).
J.-P. Celerier et al., Synthesis, 2, 130 (1981).
J.-P. Celerier et al., Tetrahedron Letters, 22, 963 (1981).

Primary Examiner—Alan M. Siegel

[57] ABSTRACT

Disclosed herein are antisecretory agents represented by the formula

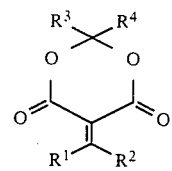

wherein $R^1$ is hydrogen and $R^2$ is lower alkylthio, (2-thienylmethyl)thio or $SCH_2$—$COOR^5$ wherein $R^5$ is hydrogen or lower alkyl, or $R^1$ and $R^2$ are independently a lower alkylthio or (2-thienylmethyl)thio, or $R^1$ and $R^2$ together with the carbon atom to which they are attached form a 2-imidazolidinylidene; and $R^3$ and $R^4$ are each the same lower alkyl, or $R^3$ and $R^4$ together with the carbon atoms to which they are attached form a cyclohexane wherein said carbon atom is a spiro atom in common with the cyclohexane ring and the adjoining dioxane ring.

17 Claims, No Drawings

ANTISECRETORY AGENTS DERIVED FROM MELDRUM'S ACID

RELATED APPLICATIONS

Related hereto are U.S. patent application Ser. Nos. 543,711 and 543,712, filed on the same date as this application.

This invention relates to novel antisecretory agents derived from Meldrum's acid (2,2-dimethyl-1,3-dioxane-4,6-dione), processes for preparing the derivatives, pharmaceutical compositions thereof, and methods for using the derivatives.

The Meldrum's acid derivatives of this invention are characterized by having a methylene substituent at position 5 of the 1,3-dioxane-4,6-dione nucleus. The methylene substituent in turn is monosubstituted or disubstituted by sulfur bearing groups, or forms part of a dependent nitrogen bearing ring.

Similar compounds have been reported by U. Herzog and H. Reinshagen, Eur. J. Med. Chem.-Chim. Ther., 11 415 (1976); F. P. Colona et al., J. Chem. Soc., Perkin Trans., 2, 279 (1978); J. Sandstrom and U. Sjostrand, Tetrahedron, 34, 371 (1978); U. Sjostrand and J. Sandstrom, Tetrahedron, 34, 3305 (1978); J.-P. Celerier et al., J. Org. Chem., 44, 3089 (1979); J.-P. Celerier et al., Synthesis, 2, 130 (1981) and J.-P. Celerier et al., Tetrahedron Letters, 22, 963 (1981).

The derivatives of the present invention can be distinguished from the previously reported compounds by the structural differences in the substitution on the methylene group, and by their uniqueness as agents for treating hyperchlorhydria, ulcers and associated conditions.

SUMMARY OF THE INVENTION

The compounds of this invention are represented by formula I

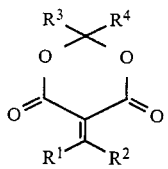

(I)

wherein $R^1$ is hydrogen and $R^2$ is lower alkylthio, (2-thienylmethyl)thio or $SCH_2COOR^5$ wherein $R^5$ is hydrogen or lower alkyl, or $R^1$ and $R^2$ are independently lower alkylthio or (2-thienylmethyl)thio, or $R^1$ and $R^2$ together with the carbon atom to which they are attached form a 2-imidazolidinylidene; and $R^3$ and $R^4$ are each the same lower alkyl, or $R^3$ and $R^4$ together with the carbon atoms to which they are attached form a cyclohexane wherein said carbon atom is a spiro atom in common with the cyclohexane ring and the adjoining dioxane ring.

A preferred group of the compounds is represented by formula I wherein $R^1$ is hydrogen or lower alkylthio and $R^2$ is lower alkylthio.

Another preferred group of compounds is represented by formula I wherein $R^1$ and $R^2$ together with the carbon atom to which they are attached form a 2-imidazolidinylidene.

A method is provided for preventing or treating gastrointestinal ulcers in a mammal, or for preventing or decreasing the secretion or availability of excessive amounts of gastric acid in a mammal suffering from hyperchlorhydria. The method comprises administering to the mammal in need thereof an effective amount of the compound of formula I.

A pharmaceutical composition in unit dosage form, for use according to the previous method, also is provided. The composition comprises the compound of formula I admixed with a pharmaceutically acceptable carrier.

The compounds of formula I are prepared by processes described hereinafter.

DETAILS OF THE INVENTION

The term "lower alkyl" as used herein means a straight chain alkyl radical containing from one to six carbon atoms or a branched chain alkyl radical containing three to six carbon atoms and includes methyl, ethyl, propyl, 1-methylethyl, butyl, 2-methylpentyl and 1,1-dimethylbutyl. Preferred lower alkyl radicals contain from one to three carbon atoms.

The term "lower alkanol" as used herein means both straight and branched chain alkanols containing from one to four carbon atoms and includes, for example, methanol, ethanol, 1-methylethanol and butanol.

The term "lower alkyl halide" as used herein means a lower alkyl halide selected from the group of lower alkyl bromides, lower alkyl chlorides and lower alkyl iodides, and includes, for example, methyl iodide, ethyl iodide and 1,1-dimethylbutyl chloride.

The term "alkali metal" as used herein means an alkali metal selected from lithium, sodium and potassium.

The compounds of formula I which are monosubstituted on the 5-methylene group (i.e. $R^1$ is hydrogen) are capable of forming tautomers. The tautomeric forms are included within the scope of this invention.

When a compound of formula I is administered to a mammal suffering from hyperchlorhydria and/or associated conditions for the purpose of preventing or decreasing the secretion of excessive amount of gastric acid or hydrochloric acid, or is used for the treatment of ulcers in mammals, it is used alone or in combination with pharmacologically acceptable carriers, the proportion of which is determined by the solubility and chemical nature of the compound, chosen route of administration and standard biological practice.

For example, the compound can be administered orally in solid form i.e. capsule or tablet, orally in liquid form, i.e. suspensions or solutions, or it can be injected parenterally. The preferred method of administration is to give it orally.

The tablet compositions can contain the compound of formula I in admixture with pharmaceutically acceptable excipients, for example, starch, milk, sugar etc. The tablets can be uncoated or they can be coated by known techniques so as to delay disintegration and adsorption in the gastrointestinal tract and thereby provide a sustained action over a longer period.

The aqueous suspensions for oral administration can contain the compound in admixture with one or more nontoxic pharmaceutical excipients known to be suitable in the manufacture of aqueous suspensions. Suitable excipients are, for example, methylcellulose, sodium alginate, gum acacia, lecithin, etc. The aqueous suspensions can also contain one or more preservatives, one or more coloring agents, one or more flavoring agents or one or more sweetening agents.

Non-aqueous suspensions for oral administration can be formulated by suspending the compound in a vegetable oil, for example, arachis oil, olive oil, sesame oil, or coconut oil, or in liquid paraffin, and the suspension may contain a thickening agent, for example, beeswax, hard paraffin or cetyl alcohol. These compositions can also contain a sweetening agent, flavoring agent or antioxidant.

For administration to a mammal by parenteral injection, it is preferred to use the compound in solution in a sterile aqueous vehicle, which may also contain other solutes such as buffers or preservatives, as well as sufficient quantities of pharmaceutically acceptable salts or of glucose to make the solution isotonic.

The dosage of the compound of formula I for combating or preventing hyperchlorhydria and/or associated conditions, or for the treatment of ulcers, in a mammal will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects. For example, an effective antiulcer amount, or an effective amount for preventing hyperchlorhydria and inhibiting hydrochloric acid secretion, of the compound usually ranges from about 1.0 mg to about 100 mg per kg of body weight per day in single or divided dose, although as aforementioned, variations will occur. However, a dosage level that is in the range from about 5.0 mg to about 50 mg per kg of body weight per day in single or divided dose is employed most desirably in order to achieve effective results.

Unit dosage forms such as capsules, tablets, syrups, suspensions and the like may contain from 10 mg to about 100 mg of the active agent of this invention with a pharmaceutical carrier.

The effectiveness of the compounds of formula I as agents for preventing hyperchlorhydria and inhibiting gastric acid secretion can be demonstrated readily in pharmacological tests. For example, the following test demonstrates their effectiveness in inhibiting spontaneous gastric acid secretion in cannulated rats.

Male albino Sprague Dawley rats (200–300 g), purchased from Canadian Breeding Laboratories, were employed. Two gastric cannulas were implanted surgically in each rat as described by L. E. Borella and F. Herr, Gastroenterology, 61, 345 (1971). The rats were used two to three weeks after the operation at a time when their food intake and weight gain were similar to the food intake and weight gain of unoperated litter mates. Before testing, the rats were deprived of food for 18 hours, but they had available a solution of 0.2% sodium chloride in 5% glucose for drinking ad libitum. Prior to each experiment, the plugs of the stomach cannulas of each rat were removed and the debris present in the stomach was flushed out with tepid saline passed through the cannulas. Thereafter, the lumen of the stomach was continuously perfused with saline introduced into the stomach through the forestomach cannula at a rate of 0.8–1.2 ml/min. The stomach perfusate flowing out of the antrum cannula was collected in 60 minutes intervals and the total acid in each collection was titrated with 0.05N sodium hydroxide employing phenol red as an indicator. After a period of acclimatization of about 60 to 90 minutes, the acid output values were recorded. On the basis of the hourly acid output, the rats were divided into equal groups so that the average acid output of all groups was similar. Saline (vehicle) or saline suspensions or solutions of the test compounds were administered intragastrically (i.g.) through the forestomach cannula, after having closed the antral cannula. During the one hour absorption period, the stomachs of the rats were not perfused. After the absorption period, perfusion of the stomachs was resumed, and the perfusates were collected hourly for three hours. The average post-treatment hourly acid outputs of the test compound groups were compared to that of the saline group and the percent inhibition of acid output was calculated. Multiple statistical comparisons between groups was done using Dunnet's t test, C. W. Dunnet, Journal of American Statistical Association, 50, 1096 (1955).

The following table shows the results obtained when compounds of formula I, listed therein, were evaluated in the preceding test.

| Compound of Formula I | | | | Example in Which Compound is Prepared | Percent Inhibition of Acid Output (25 mg/kg/i.g.) |
| --- | --- | --- | --- | --- | --- |
| $R^1$ | $R^2$ | $R^3$ | $R^4$ | | |
| H | $SC_2H_5$ | $CH_3$ | $CH_3$ | 1 | 79 |
| $SCH_3$ | $SCH_3$ | $CH_3$ | $CH_3$ | 3 | 73 |
| $SCH_3$ | $SCH_3$ | $C_2H_5$ | $C_2H_5$ | 3 | 74 |
| $SCH_3$ | $SCH_3$ | —$(CH_2)_4$— | | 3 | 47 |
| —$NHCH_2CH_2NH_2$— | | $CH_3$ | $CH_3$ | 7 | 25 |

The beneficial effect of the compounds of formula I on gastrointestinal ulcer formation can be demonstrated by assessing their effects on gastric lesions induced in rats by absolute alcohol according to the method of A. Robert et al., Gastroenterology, 77, 433 (1979).

Process

The compounds of formula I wherein $R^1$, $R^2$, $R^3$ and $R^4$ are as defined herein can be prepared by a process comprising:

(a) reacting a compound of formula II

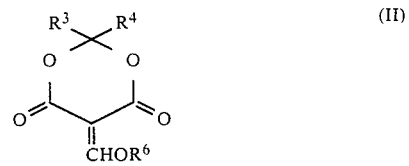

wherein $R^3$ and $R^4$ are as defined herein and $R^6$ is hydrogen or lower alkyl with a mercaptan of formula $R^7SH$ wherein $R^7$ is lower alkyl, 2-thienylmethyl or $CH_2COOR^5$ wherein $R^5$ is hydrogen or lower alkyl to obtain the corresponding compound of formula I wherein $R^1$ is hydrogen, $R^2$ is lower alkylthio, (2-thienylmethyl)thio or $SCH_2COOR^5$ wherein $R^5$ is hydrogen or lower alkyl and $R^3$ and $R^4$ are as defined herein; or (b) reacting a compound of formula III

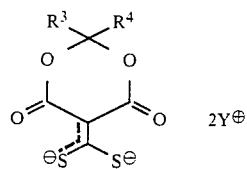

wherein $R^3$ and $R^4$ are as defined herein and Y is an alkali metal cation with a lower alkyl halide to obtain the corresponding compound of formula I wherein $R^1$ and $R^2$ are each the same lower alkylthio and $R^3$ and $R^4$ are as defined herein; or (c) reacting a first compound of formula I wherein $R^1$ and $R^2$ are each the same lower alkylthio and $R^3$ and $R^4$ are as defined herein with at least three molar equivalents of a lower alkylmercaptan wherein the lower alkylthio portion is different from the lower alkylthio of $R^1$ and $R^2$ of said first compound of formula I to obtain the corresponding second compound of formula I in which $R^1$ and $R^2$ are each different lower alkylthio, one lower alkylthio corresponding to the lower alkylthio of $R^1$ and $R^2$ of the first compound of formula I and the other lower alkylthio corresponding to lower alkylthio portion of the lower alkylmercaptan, and/or the corresponding third compound of formula I in which $R^1$ and $R^2$ are each the same lower alkylthio which also corresponds to the lower alkylthio portion of the lower alkylmercaptan; or (d) reacting the compound of formula I wherein $R^1$ and $R^2$ are each the same lower alkylthio and $R^3$ and $R^4$ are as defined herein with at least three molar equivalents of (2-thienylmethyl)mercaptan to obtain the corresponding compound of formula I wherein $R^1$ is lower alkyl and $R^2$ is (2-thienylmethyl)thio and $R^3$ and $R^4$ are as defined herein, and/or the compound of formula I wherein $R^1$ and $R^2$ are each (2-thienylmethyl)thio and $R^3$ and $R^4$ are as defined herein; or (e) reacting the compound of formula I wherein $R^1$ and $R^2$ are each the same lower alkylthio and $R^3$ and $R^4$ are as defined herein with 1,2-ethanediamine to obtain the compound of formula I wherein $R^1$ and $R^2$ together with the carbon atom to which they are attached form a 2-imidazolidinylidene.

The starting materials of formula II are either known or can be prepared by known methods from the corresponding 2,2-disubstituted-1,3-dioxane-4,6-diones. For example, 5-(hydroxymethylene)-2,2-dimethyl-1,3-dioxane-4,6-dione and 5-(methoxymethylene)-2,2-dimethyl-1,3-dioxane-4,6-dione have been prepared from 2,2-dimethyl-1,3-dioxane-4,6-dione; see G. A. Bihlmayer et al., Monastsh. Chem., 98, 564 (1967).

The starting materials of formula III are prepared by reacting the appropriate 2,2-disubstituted 1,3-dioxane-4,6-dione with carbon disulfide under anhydrous conditions in the presence of a suitable alkali metal hydride, for instance, sodium hydride, or an alkali metal(lower-)alkoxide, for instance sodium methoxide or potassium ethoxide.

More explicitly, and firstly with reference to paragraph (a) of the above statement itemizing the process for preparing the compounds of formula I, the compounds of formula I wherein $R^1$ is hydrogen, $R^2$ is lower alkylthio, (2-thienylmethyl)thio or $SCH_2COOR^5$ wherein $R^5$ is hydrogen or lower alkyl, and $R^3$ and $R^4$ are as defined herein can be prepared by reacting the 5-(hydroxymethylene) or 5-(lower alkoxymethylene) compound of formula II with at least one, preferably two to six molar equivalents, of the mercaptan of formula $R^7SH$ wherein $R^7$ is lower alkyl, 2-thienylmethyl or $CH_2COOR^5$ wherein $R^5$ is hydrogen or lower alkyl. The reaction is most conveniently done in an inert solvent. Suitable inert solvents include the lower alkanols, dioxane, toluene or benzene. Although the optimum temperature and reaction times will vary, depending on the reactants employed, the reaction usually is done at 20° to 100° C., or at the boiling point of the reaction mixture, for 10 minutes to six hours. Generally, the ideal reaction time can be determined by thin layer chromatography of aliquots removed from the reaction mixture during the course of the reaction.

With reference to paragraph (b) of the above statement, the compounds of formula I wherein $R^1$ and $R^2$ are each the same lower alkyl and $R^3$ and $R^4$ are as defined herein can be prepared by reacting the di(alkali metal) salt of the ketenethioacetal of formula III with about two to five molar equivalents of a lower alkyl halide in an inert solvent under anhydrous conditions. Suitable inert solvents for this reaction include dimethylformamide, acetonitrile, benzene tetrahydrofuran and toluene. The preferred di(alkali metal) salts of formula III are those having sodium or potassium cations (i.e. Y=Na or K).

For convenience, the preceding reaction can be performed in the medium used to prepare the di(alkali metal) salt. Thus, a practical and convenient method of accomplishing this reaction involves preparing the di(alkali metal) by reacting the appropriate 2,2-disubstituted-1,3-dioxane-4,6-dione with about two molar equivalents of carbon disulfide in the presence of two to four molar equivalents of sodium hydride in dimethylformamide or benzene, or a mixture of the latter two solvents. In this manner, the disodium salt of the ketenethioacetal of formula III is formed usually within 30 minutes to about two hours at room temperature. Thereafter, the medium containing the disodium salt is subjected to the addition of about four molar equivalents of the appropriate lower alkyl halide at temperatures ranging from 0° to 25° C., followed by heating the reaction mixture at 30° to 60° C. for an hour to complete the reaction. Conventional work up of the reaction mixture then affords the desired compound of formula I in which $R^1$ and $R^2$ are each the same lower alkylthio and $R^3$ and $R^4$ are as defined herein, "a first compound of formula I".

With reference to paragraph (c) of the above statement, compounds of formula I in which each of $R^1$ and $R^2$ is a different lower alkylthio, or compounds of formula I in which $R^1$ and $R^2$ are the same lower alkylthio (but different from the lower alkylthio groups of the compound of formula I from which they are derived) can be prepared by an exchange reaction wherein one or both lower alkylthios are replaced by other lower alkylthios to give the "second" or "third" compound of formula I, respectively. According to this procedure, the aforementioned first compound of formula I, obtained as described in paragraph (b) and having the same lower alkylthio for $R^1$ and $R^2$, is brought into contact with a large excess of a lower alkylmercaptan having a lower alkylthio portion different from that of the $R^1$ and $R^2$ of said first compound of formula I. The reaction is best accomplished by dissolving the first compound of formula I and three to about 20 molar equivalents of the lower alkylmercaptan in an inert solvent and allowing the exchange of alkylthio(s) to proceed until a preponderance of the desired product is present in the reaction mixture, as judged by thin layer chromatography examination of an aliquot of the reaction mixture. Suitable solvents for this reaction include the lower alkanols, toluene benzene, dioxane and the like.

The reaction can best be achieved by conducting the reaction in the presence of at least two molar equivalents of an alkali metal lower alkoxide, for example, sodium methoxide or potassium ethoxide.

Although the optimum temperatures and reaction times will vary depending on the reactants employed and whether one or two lower alkylthios are to be replaced, the reaction usually is completed within 10 minutes to about four hours at temperatures ranging from 20° to 80° C. The longer the reaction time and the higher the reaction temperature, the more favored is the formation of the third compound of formula I with the same lower alkylthios for $R^1$ and $R^2$, which are different from the lower alkylthios of the starting material of formula I. Conversely, a preponderance of the second compound can be realized by a shorter reaction time and lower reaction temperatures. Chromatography can be used to separate product mixtures of the second and third compounds.

With reference to paragraph (d), the compounds of formula I wherein $R^1$ is lower alkylthio, $R^2$ is (2-thienylmethyl)thio and $R^3$ and $R^4$ are as defined herein (such a compound is designated hereinafter as "the fourth compound of formula I") and the compounds of formula I wherein $R^1$ and $R^2$ are each (2-thineylmethyl)thio and $R^3$ and $R^4$ are as defined herein (such a compound is designated hereinafter as the fifth compound) can be prepared also by an exchange type of reaction. Thus, the fourth and fifth compounds of formula I are obtained by reacting a compound of formula I wherein $R^1$ and $R^2$ are each the same lower alkylthio and $R^3$ and $R^4$ are as defined herein with three to six molar equivalents of (2-thienylmethyl)mercaptan. The reaction can be performed by simply mixing the two reactants together and heating the mixture. Optionally an inert solvent, for instance benzene, toluene, tetrahydrofuran or a lower alkanol, may be employed as a reaction medium. The reaction usually is conducted at temperatures ranging from 35° to 80° C. for 30 minutes to four hours. However, depending on whether the fourth compound or the fifth compound is desired, the reaction times and temperature are varied. The longer the reaction time and the higher the temperature, the better the yield of the fifth compound of formula I in which $R^1$ and $R^2$ are both (2-thienylmethyl)thio. Conversely, a shorter reaction time and a lower temperature are employed if the fourth compound of formula I is the desired product. The course of the reaction can be followed by thin layer chromatography examination of aliquots, removed periodically, from the reaction mixture. Chromatography can be used to separate product mixtures of the fourth and fifth compounds.

With reference to section (e) compounds of formula I wherein $R^1$ and $R^2$ together with the carbon atom to which they are attached form a 2-imidazolidinylidene and $R^3$ and $R^4$ are as defined herein, are obtained by reaction the compound of formula I in which $R^1$ and $R^2$ are each lower alkylthio and $R^3$ and $R^4$ are as defined herein with one to three molar equivalents of 1,2-ethanediamine. The reaction is performed best at temperatures ranging from 40° to 100° C. for 30 minutes to four hours using an inert solvent, for instance, one of the lower alkanols, as a reaction medium.

The following examples further illustrate this invention.

EXAMPLE 1

5-[(Ethylthio)methylene]-2,2-dimethyl-1,3-dioxane-4,6-dione (I; $R^1=H$, $R^2=SC_2H_5$ and $R^3$ and $R^4=CH_3$)

5-(Methoxymethylene)-2,2-dimethyl-1,3-dioxane-4,6-dione (7 g, 38 mmole), described by Bihlmayer et al., supra, was suspended in ethanol (70 ml). The suspension was stirred vigorously while being subjected to the addition of ethanethiol (12.85 g, 200 mmole). The mixture was heated at reflux until all the starting material had been consumed, as indicated by thin layer chromatography (silica gel plates, 30% ethyl acetate in hexane). The volatile portion of the reaction mixture was removed by distillation under reduced pressure. The residue was purified by high pressure liquid chromatography (HPLC, 20% ethyl acetate in hexane, v/v). The purest fractions were combined. The solvent was removed under reduced pressure. The residue was crystallized to give 5.0 g of the title compound; mp 52°–54° C.; NMR (CDCl$_3$) δ 1.45 (t, 3H), 1.7 (s, 6H), 3.02 (q, 2H), 9.0 (s, 1H); IR (CHCl$_3$) 1720, 1700 cm$^{-1}$.

In the same manner, but replacing ethanethiol with an equivalent amount of 2-thiophenemethanethiol, described by P. Cagniant, Compt. rend., 229, 1342 (1949), 2,2-dimethyl-5-[[(2-thienylmethyl)thio]methylene]-1,3-dioxane-4,6-dione (I; $R^1=H$, $R^2=$(2-thienylmethyl)thio, and $R^3$ and $R^4=CH_3$) was obtained; mp 109°–111° C. (after crystallization from ethyl acetate); NMR (CDCl$_3$) δ1.67 (s, 6H), 4.36 (s, 2H), 6.95 (m, 2H), 7.20 (m, 1H), 8.95 (s, 1H); IR (CHCl$_3$) 1730, 1705, 1525 cm$^{-1}$; UVλmax (MeOH) 322 nm (ε8340), 237 (12,900); was obtained.

EXAMPLE 2

[[(2,2-Dimethyl-4,6-dioxo-1,3-dioxan-5-ylidene)methyl]thio]acetic acid, methyl ester (I; $R^1=H$, $R^2=SCH_2COOCH_3$, and $R^3$ and $R^4=CH_3$)

A mixture of 5-(hydroxymethylene)-2,2-dimethyl-1,3-dioxane-4,6-dione (8.6 g, 50 mmole), described by Bihlmayer et al., supra, and mercaptoacetic acid methyl ester (13 g, 0.125 mole) in dry methanol (50 mL) was heated at reflux for 2 hr. Thereafter, the mixture was stirred for 18 hr at 20°–22° C., and then poured into ice-water. The resultant mixture was extracted with diethyl ether. The extract was dried (MgSO$_4$) and concentrated to dryness under reduced pressure. The residue (8.0 g) was purified by chromatography on silica gel, using 30% ethyl acetate in hexane (v/v) as the eluant. The pure fractions were combined and the solvent removed under reduced pressure. Crystallization of the residue from ethyl acetate-hexane gave the title compound; mp 117°–118° C.; NMR (CDCl$_3$) δ 1.7 (s, 6H), 3.65 (s, 2H), 3.75 (s, 3H), 8.95 (s, 1H); IR (CHCl$_3$) 1735, 1700, 1535 cm$^{-1}$; UVλmax (MeOH) 315 um (ε 8900), 260 (7950).

In the same manner, but replacing mercaptoacetic acid methyl ester with mercaptoacetic acid, [[(2,2-dimethyl-4,6-dioxo-1,3-dioxan-5-ylidene)methyl]-thio]acetic acid is obtained.

EXAMPLE 3

5-[bis(Methylthio)methylene]-2,2-dimethyl-1,3-dioxane-4,6-dione (I: $R^1$ and $R^2 = SCH_3$, and $R^3$ and $R^4 = CH_3$)

A solution of 2,2-dimethyl-1,3-dioxane-4,6-dione (8.1 g, 56 mmole) in dry benzene (30 mL) and distilled dimethylformamide (10 mL) was added dropwise under nitrogen to a well stirred suspension of sodium hydride (5.4 g, 110 mmole, 50% in mineral oil in dry benzene (25 mL) at 20°-22° C. (room temperature). The reaction mixture was cooled to 10° C. Carbon disulfide (8.6 g, 6.8 mL, 110 mmole) was added dropwise followed by distilled dimethylformamide (25 mL). After the addition, the mixture was heated at 46° C. for 2 hr, during which time the color of the mixture turned deep red. After cooling to 10° C., methyl iodide (15.9 g, 7 mL, 11 mmoles) was added dropwise to the mixture. Stirring was continued at 20°-22° C. for 18 hr. The mixture was poured into ice water and extracted with ethyl acetate. The combined extracts were washed with water, brine and dried ($MgSO_4$). The solvent was removed under reduced pressure. The oily residue was dissolved in ethyl acetate (50 mL) and the solution was added to hexane (225 mL). The precipitated solid was collected, dried (2.7 g) and recrystallized from ethyl acetate-hexane to give 1.2 g of the title compound; mp 114°-118° C.; NMR ($CDCl_3$) δ 1.25 (s, 6H), 2.65 (s, 6H); IR ($CHCl_3$) 1580 $cm^{-1}$; UVλmax (MeOH) 347 nm (ε 12,500), 220 (7470).

In the same manner, but replacing 2,2-dimethyl-1,3-dioxane-4,6-dione with an equivalent amount of 2,2-diethyl-1,3-dioxane-4,6-dione, described by G. Y. Lesher and C. J. Opalka, U.S. Pat. No. 4,104,385, Aug. 1, 1978, 2,2-diethyl-5-[bis(methylthio)methylene]-1,3-dioxane-4,6-dione (I; $R^1$ and $R^2 = SCH_3$ and $R^3$ and $R^4 = C_2H_5$) was obtained. The latter compound had 88.5°-90° C.; NMR ($CDCl_3$) δ 1.0 (t, 6H), 1.95 (3t, 4H), 2.6 (s, 6H); IR ($CHCl_3$) 1715, 1680 $cm^{-1}$.

In the same manner, but replacing 2,2-dimethyl-1,3-dioxane-4,6-dione with an equivalent amount of 1,5-dioxaspiro[5.5]undecane-2,4-dione, described by I. N. Khaimov et al., Fiziol. Aktivn. Veshchestva, Resp. Mezhved. Sb., (10), 70 (1978); see Chem. Abstr., 90, 203984e (1979), 3-[bis(methylthio)methylene]-1,5-dioxaspiro[5.5]undecane-2,4-dione (I; $R^1$ and $R^2 = SCH_3$, and $R^3$ and $R^4$ together are $-(CH_2)_4-$) was obtained. The latter compound had mp 123°-125° C.; NMR ($CDCl_3$) δ 1.6 (m, 6H), 1.95 (m, 4H), 2.6 (s, 6H); IR($CHCl_3$) 1710, 1685 $cm^{-1}$; UVλmax ($CH_3OH$) 347 nm (ε 13,900), 220(7440).

EXAMPLE 4

5-[bis(Ethylthio)methylene]-2,2-dimethyl-1,3-dioxane-4,6-dione (I; $R^1$ and $R^2 = SC_2H_5$, and $R^3$ and $R^4 = CH_3$)

A solution of 5-[bis(methylthio)methylene]-2,2-dimethyl-1,3-dioxane-4,6-dione (2.3 g, 9.2 mmole, described in example 3), ethanethiol (8.4 g, 10 mL, 135 mmole) and sodium methoxide (480 mg, 20.7 mmole) in dry methanol (12 mL) was stirred at 20°-22° C. for 30 min. The solution was poured into ice water. The resultant mixture was extracted with ethyl acetate. The combined extracts were washed with water, dried ($MgSO_4$) and concentrated to dryness under reduced pressure. The residue was purified by HPLC (20% ethyl acetate in hexane, v/v). The purest fractions were combined. The solvent was removed under reduced pressure to give 0.59 g of the title compound as an oil; NMR ($CDCl_3$) δ 1.36 (t, J=7 Hz, 6H), 1.72 (s, 6H), 3.11 (3t, J=7 Hz, 4H); IR ($CHCl_3$) 1715 $cm^{-1}$; UVλmax (MeOH) 345 nm (ε 13,040), 215 (8160).

EXAMPLE 5

2,2-Dimethyl-5-[bis(2-thienylmethyl)thio]methylene]-1,3-dioxane-4,6-dione (I; $R^1$ and $R^2 = $(2-thienylmethyl)thio, and $R^3$ and $R^4 = CH_3$)

A mixture of 2-thiophenemethanethiol (9.4 g, 73 mmole) and 5-[bis(methylthio)methylene]-2,2-dimethyl-1,3-dioxane-4,6-dione (6 g, 24 mmole, described in example 3) was heated at 50° C. under nitrogen for one hr. Excess mercaptan was removed by distillation in high vacuum. The residue was purified by chromatography on a silica gel column, using 25% ethyl acetate in hexane (v/v) as the eluant. The pure fractions were pooled. The solent was removed under reduced pressure. The residue was crystallized from chloroform-hexane to give 1.6 g of the title compound; mp 110°-112° C.; NMR ($CDCl_3$) δ 1.65 (s, 6H), 4.55 (s, 4H), 7.05 (m, 6H); IR ($CHCl_3$) 1715, 1685 $cm^{-1}$; UVλmax (MeOH) 346 nm (ε 15,200), 232 (21,200).

EXAMPLE 6

2,2-Dimethyl-5-[[methylthio[(2-thienylmethyl)thio]methylene]-1,3-dioxane-4,6-dione (I; $R^1 = CH_3S$, $R^2 = $(2-thienylmethyl)thio, and $R^3$ and $R^4 = CH_3$)

A mixture of 2-thiophenemethanethiol (4.72 g, 36 mmole) and 5-[bis(methylthio)methylene]-2,2-dimethyl-1,3-dioxane-4,6-dione (3 g, 12 mmole, described in example 3) was stirred at 20°-22° C. for one hr, and then heated at 50° C. for one hr. The cooled mixture was poured through a column of silica gel. The column was eluted with 20% ethyl acetate in hexane (v/v). The fractions contained two products as indicated by thin layer chromatography ($SiO_2$, 50% hexane in ethyl acetate, v/v), mainly the desired product plus the bis[(2-thienylmethyl)thio] analog of example 4. The fractions were combined and evaporated to dryness. The residue was subjected to chromatography on silica gel using 25% ethyl acetate in hexane (v/v). The purest fractions were combined and evaporated. The residue was crystallized from ethyl acetate-hexane to give 1.8 g of the title compound; mp 142°-144° C.; NMR ($CDCl_3$) δ 1.69 (s, 6H), 2.52 (s, 3h), 4.54 (s, 2H), 6.95 (m, 2H), 7.25 (s, 1H); IR ($CHCl_3$) 1715, 1685 $cm^{-1}$; UVλmax (MeOH) 345 (ε 14,000), 227 (13,000).

EXAMPLE 7

5-(2-Imidazolidinylidene)-2,2-dimethyl-1,3-dioxane-4,6-dione (I; $R^1$ and $R^2 = -NH-(CH_2)_2NH-$, and $R^3$ and $R^4 = CH_3$)

1,2-Ethanediamine (1.6 mL) was added under nitrogen to a solution of 5-[bis(methylthio)methylene]-2,2-dimethyl-1,3-dioxane-4,6-dione (6 g, 24 mmole, described in example 3) in dry methanol (45 mL). The mixture was stirred at 20°-22° C. for 18 hr. The resultant precipitate was collected and dissolved in 5% methanol in chloroform (v/v). The solution was filtered through silica gel. The filtrate was concentrated under reduced pressure. The residue was crystallized from methanol-diethyl ether to give 4.4 g of the title compound; mp 181°-182° C.; NMR ($CDCl_3$) δ 1.65 (s, 6H), 3.8 (s, 4H), 8.25 (m, 2H); IR ($CHCl_3$) 3350, 1690, 1660, 1645, 1590 $cm^{-1}$; UVλmax (MeOH) 243 nm (ε 25,500).

We claim:

1. A compound of formula I

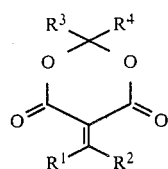

wherein $R^1$ is hydrogen and $R^2$ is lower alkylthio, (2-thienylmethyl)thio or $SCH_2$—$COOR^5$ wherein $R^5$ is hydrogen or lower alkyl, or $R^1$ and $R^2$ are each independently lower alkylthio or (2-thienylmethyl)thio, or $R^1$ and $R^2$ together with the carbon atom to which they are attached form a 2-imidazolidinylidene; and $R^3$ and $R^4$ are each the same lower alkyl or $R^3$ and $R^4$ together with the carbon atom to which they are attached form a cyclohexane ring wherein said carbon atom is a spiro atom in common with the cyclohexane ring and the adjoining dioxane ring.

2. The compound of claim 1 wherein $R^1$ is hydrogen or lower alkylthio and $R^2$ is lower alkylthio.

3. The compound of claim 1 wherein $R^1$ and $R^2$ together with the carbon atom to which they are attached form a 2-imidazolidinylidene.

4. The compound of claim 2, which is 5-[(ethylthio)-methylene]-2,2-dimethyl-1,3-dioxane-4,6-dione.

5. The compound of claim 1, which is 2,2-dimethyl-5-[[(2-thienylmethyl)thio]methylene]-1,3-dioxane-4,6-dione.

6. The compound of claim 1, which is [[(2,2-dimethyl-4,6-dioxo-1,3-dioxan-5-ylidene)methyl]thio]acetic acid, methyl ester.

7. The compound of claim 2, which is 5-[bis(methylthio)methylene]-2,2-dimethyl-1,3-dioxane-4,6-dione.

8. The compound of claim 2, which is 2,2-diethyl-5-[bis(methylthio)-methylene]-1,3-dioxane-4,6-dione.

9. The compound of claim 2, which is 3-[bis(methylthio)methylene]-1,5-dioxaspiro[5.5]undecane-2,4-dione.

10. The compound of claim 2, which is 5-[bis(ethylthio)methylene]-2,2-dimethyl-1,3-dioxane-4,6-dione.

11. The compound of claim 1, which is 2,2-dimethyl-5-[bis[(2-thienylmethyl)thio]methylene]-1,3-dioxane-4,6-dione.

12. The compound of claim 1, which is 2,2-dimethyl-5-[[methylthio-[(2-thienylmethyl)thio]methylene]-1,3-dioxane-4,6-dione.

13. The compound of claim 3, which is 5-(2-imidazolidinylidene)-2,2-dimethyl-1,3-dioxane-4,6-dione.

14. A pharmaceutical composition in unit dosage form for preventing or treating gastrointestinal ulcers in a mammal, which comprises an effective amount of a compound of claim 1 and a pharmaceutically acceptable carrier.

15. A pharmaceutical composition in dosage unit form for suppressing gastric acid secretions in a mammal, which comprises an effective amount of a compound of claim 1 and a pharmaceutically acceptable carrier.

16. A method for preventing or treating gastrointestinal ulcers in a mammal, which comprises administering to the mammal in need thereof an effective amount of a compound of claim 1.

17. A method for preventing or decreasing the secretion or availability of excessive amounts of gastric acid in a mammal suffering from hyperchlorhydria, which comprises administering to the mammal in need thereof an effective amount of a compound of claim 1.

* * * * *